United States Patent
Allen

(10) Patent No.: US 6,914,051 B1
(45) Date of Patent: Jul. 5, 2005

(54) PENETRATING ANTIBIOTIC GEL FOR SOFT TISSUE DISEASES

(76) Inventor: David M Allen, Orthopaedic Surgery, 27871 Medical Center Rd., Suite 110, Mission Viejo, CA (US) 92691

( * ) Notice: Subject to any disclaimer, the term of this patent is extended or adjusted under 35 U.S.C. 154(b) by 62 days.

(21) Appl. No.: 09/896,368

(22) Filed: Jun. 28, 2001

Related U.S. Application Data

(60) Provisional application No. 60/214,809, filed on Jun. 28, 2000.

(51) Int. Cl.$^7$ ............... A61K 31/7048; A61K 9/06; A61K 9/10; A61K 9/127; A61K 9/00

(52) U.S. Cl. ............... 514/29; 514/27; 514/28; 514/30; 514/31; 514/450; 514/763; 514/769; 514/772; 514/772.3; 514/774; 514/777; 514/778; 514/781; 514/782; 514/825; 514/886; 514/887; 514/937; 514/944; 514/946; 424/400; 424/450; 424/484; 424/486; 424/488

(58) Field of Search ............... 514/27–31, 450, 514/763, 769, 772, 772.3, 774, 777, 778, 781, 782, 825, 886, 887, 937, 944, 946, 12, 78, 210.02; 424/400, 450, 484, 486, 488, 94.63, 9.3

(56) References Cited

U.S. PATENT DOCUMENTS

| | | | | |
|---|---|---|---|---|
| 5,560,910 A | * | 10/1996 | Crandall | 424/94.63 |
| 5,723,447 A | * | 3/1998 | Macy et al. | 514/29 |
| 6,239,113 B1 | * | 5/2001 | Dawson et al. | 514/29 |
| 6,281,199 B1 | * | 8/2001 | Gupta | 514/29 |

FOREIGN PATENT DOCUMENTS

| | | | |
|---|---|---|---|
| WO | 95/09601 | * | 4/1995 |

OTHER PUBLICATIONS

Chemical Abstracts 132:69251 (1999).*
Oh, Yu–Kyoung et al., "Formulation and efficacy of liposome–encapsulated antibiotics for therapy of intracellular Mycobacterium avium infection," Antimicrobial Agents and Chemotherapy, vol. 39, No. 9, Sep. 1995, pp. 2104–2111.*
Chemical Abstracts 85:87225 (1976).*
Steadman's Medical Dictionary, 26$^{th}$ ed., Williams & Wilkins, Baltimore, 1995, p. 1692.*
Dorland's Illustrated Medical Dictionary, 30$^{th}$ ed., Saunders, 2003, pp. 803 and 1840.*
Chemical Abstracts 100:73895 (1984).*
Backman et al. (Abstract only) Zeitschrift fur Rheumatologie—Nov.–Dec. 1983.

* cited by examiner

*Primary Examiner*—John Pak
(74) *Attorney, Agent, or Firm*—Todd N. Hathaway

(57) ABSTRACT

A penetrating antibiotic gel for treating pain, inflammation and other pathological conditions affecting musculoskeletal tissues and other soft tissues of the body. The composition includes an antibiotic compound and a mobilizing agent in an amount sufficient to enable the antimicrobial compound to penetrate into the sub-dermal soft tissues. The antimicrobial compound may be a macrolide antibiotic compound such as azithromycin, erythromycin or roxithromycin, for example, and the mobilizing agent may be an organogel compound, such as pluronic lecithin liposomal organogel (PLO). The composition may further include a penetration enhancing adjuvant, such as d-limonene, for example. The composition may be applied topically so as to penetrate into the sub-dermal soft tissues, or may injected so as to be absorbed into the soft tissues locally.

31 Claims, No Drawings

PENETRATING ANTIBIOTIC GEL FOR SOFT TISSUE DISEASES

This application claims the benefit of Provisional Application 60/214,809, filed on Jun. 28, 2000.

BACKGROUND OF THE INVENTION a. Field of the Invention

The present invention relates generally to methods for treatment of soft tissue diseases, and, more particularly, to a therapy for treatment of soft tissue disease states and related conditions by application of a combination of an antibiotic agent and a mobilizing gel or other carrier for penetrating the tissue.

b. Background and Related Art

As used herein, the term "soft tissue disease" refers to inflammations and other pathological conditions affecting musculoskeletal tissues and other soft tissues of the body, which are referred to from time to time herein as sub-dermal tissues so as to distinguish them from dermal conditions. Just a few examples of such conditions involving musculoskeletal tissues include tendonitis, synovitis, tenosynovitis, myositis and arthritis. Such conditions may develop naturally or may be the result of strain or other trauma, and typically manifest themselves in the form of pain, stiffness, and similar symptoms.

As part of the present invention, it is hypothesized that some such soft tissue disease conditions may either result from or be aggravated by chronic or acute microbial infections involving the affected tissues. Research has correlated a high incidence of Mycoplasma to tendonitis and synovitis in poultry, and has shown the relationship between the presence of members of the Mycoplasma or Chlamydia families and other soft tissue diseases in poultry and other animals. Other research has demonstrated that Mycoplasmas are associated with the development of arthritis in swine and poultry (e.g., see Backman et al., *Zeitschrift fur Rheumatologie*, November-December 1983).

Data relating the presence of Mycoplasma/Chlamydia to soft tissue disease in humans is less available, owing in part to the relative difficulty of obtaining samples of tissue for analysis. Nevertheless, the scientific literature includes a number of studies documenting a high detection rate for bacterial DNA in certain types of human musculoskeletal disease, notably in arthritic joint fluid. It has also been found that many cases of severe acute lower back pain respond dramatically (e.g., overnight) to short-term treatment with an oral antibiotic specific to Chlamydia Pneumoniae, namely azythromycin. Three or so days following onset of the back symptoms, however, this effect was not seen. These observations are significant in that they are in keeping with the microbiology of Chlamydia Pneumoniae, which immediately after initial infection produces an abundance of lactic acid that is locally quite painful, and three days later produces a substance called Chlamydia Specific Heat Shock Protein (HSP), or HSP60 or HSP10. This substance causes the affected cells to produce altered lipids which are flammatory and atherogenic.

This same basic sequence of infection has been seen to occur in other organs and systems in the body, including in connection with the coronaries, carotid arteries and aortic aneurysms. Other research, particularly in Europe, has provided evidence regarding the involvement of Chlamydia Pneumoniae infections in arteriosclerosis, and these same bacteria has been strongly implicated in Alzheimer's Disease and multiple sclerosis.

As part of the present invention, Applicant has found that a large number of patients receiving orthopedic treatment for chronic severe lower back pain or tendonitis test positive for Chlamydia Pneumoniae, either by positive PCR (bacterial gene detection) of the peripheral blood or by specific serum antibodies to C. Pneumoniae. By way of background, it will be understood that Chlamydia Pneumoniae is a pathogenic obligate intracellular bacteria infecting through the upper respiratory system, which is responsible for approximately 5% of ambulatory pneumonia. It is not to be confused with Chlamydia Trachomatis, a totally different bacteria which is sexually transmitted and responsible largely only for genitourinary and ocular pathology.

In view of this evidence, Applicant has developed the non-binding hypothesis that one or more infectious microorganisms, in particular, members of the Mycoplasma or Chlamydia families, may be responsible for precipitating or aggravating many forms of soft tissue disease, including musculoskeletal disease, and/or the pain and other symptoms which are associated therewith. As part of Applicant's hypothesis it is believed that the microbial activity takes place within the affected soft tissues themselves, and it is therefore a primary object of the present invention to provide a method by which the affected soft tissues are penetrated with a suitable antimicrobial agent so as to control or eradicate the infection at its origin.

As was noted above, some of these conditions (namely, chronic severe lower back pain) have responded to antibiotics that have been administered orally. While this may represent a suitable form of treatment in some instances, certain drawbacks inherent in the oral administration of antibiotics tend to limit the effectiveness of this approach. For example, oral administration of antibiotics can cause significant and sometimes life-threatening gastrointestinal side effects, especially in the case of the elderly and when administered in high dosages and over extended periods. Furthermore, oral administration of antibiotics can provide only systemic treatment, with no specificity as to the location of action, and is also comparatively slow in effect.

Antibiotics may also be administered by injection or intravenously, however, with conventional techniques the effect is again systemic rather than localized, and in any event such an approach is not normally suitable for home or self-administered treatment. Topical administration of antibiotics has also been proposed or used in some instances, but with penetration by the antibiotic being limited to the dermis, typically for treatment of acne, cuts, burns, infections, baldness, or other skin conditions or damage; such dermal applications would do nothing to reach and treat the sub-dermal soft tissue diseases described above.

Accordingly, there exists a need for a method and composition for treatment of soft tissue diseases and related conditions and disease states, by administration of one or more antimicrobial agents so as to control or eradicate microbial activity in the affected area. Furthermore, there exists a need for such a method and composition which avoid the gastrointestinal hazards and other side effects associated with oral administration of antibiotics. Still further, there exists a need for such a method and composition that permit treatment to be limited to a specific location or locations within the body. Still further, there exists a need for such a method and composition that provide quick penetration and action so as to minimize microbial progress in the affected area.

SUMMARY OF THE INVENTION

Applicant has now developed methods and compositions (combinations and formulations) for locally controlling or eradicating microbial infection of soft tissue areas so as to alleviate the resulting disease states and/or conditions. Broadly, the method comprises the steps of compounding an antimicrobial compound with a mobilizing agent in predetermined amounts, and applying the compounded combination to the involved area so that the mobilizing agent enables the antimicrobial compound to penetrate deeply into the soft tissue and attack the microbial infection therein.

The antimicrobial compound may be an antibiotic, and the antibiotic may be selected to control or eradicate a microbial infection of a predetermined type. The antibiotic may be azythromicin, for controlling or eradicating Chlamydia Pneumoniae and/or Mycoplasma-family pathogens in the affected soft tissue. The disease state may be a musculoskeletal disease that is caused or aggravated by the Chlamydia Pneumoniae and/or Mycoplasma infection.

The mobilizing agent may be a penetrating gel. The penetrating gel may be Pleuronic Lecithin Liposomo Organogel (PLO). Azythromicin may be compounded with the PLO gel in a predetermined amount from about 50 mg per 1 cc to about 3 g per 1 cc so as to form a gel mixture for topical application. The predetermined amount of azythromicin may be approximately 250 mg per 1 cc of PLO, to prepare a gel mixture for topical application three times a day.

The compounded antimicrobial compound and mobilizing agent may be applied topically, so that the mobilizing agent enables the antimicrobial compound to penetrate through the skin and into the underlying soft tissue area Alternatively, the composition may be administered by injection, or intravenously or intrathecally (i.e., into the spinal fluid). The soft tissue being treated may be musculoskeletal tissue, or may be tissue of the cardiovascular or central nervous systems or other systems of the body.

The compositions and methods of the present invention may be employed for human or animal therapy.

The present invention and features and advantages thereof will be better understood by a reading of the detailed description provided below.

DETAILED DESCRIPTION a. Overview

The present invention provides a therapy for treatment for musculoskeletal disease and other soft tissue diseases, by localized application of a combination of an antimicrobial compound and a mobilizing agent which is selected to penetrate the soft tissues, so that the antimicrobial agent rapidly penetrates the tissues and attacks the suspected microbial infection in the affected area.

A preferred mobilizing agent is a penetrating organic hydrogel, with Pleuronic Lecithin Liposomal Organogel (PLO) being most preferred for many applications. The antibiotic is preferably specific to the target microorganism, with azithromycin being preferable for treatment of conditions believed to involve members of the Mycoplasma or Chlamydia families.

The therapeutic composition may be applied topically so as to penetrate the underlying soft tissues for localized inflammations. The composition is compounded to include the antibiotic and mobilizing agent in sufficient amounts to penetrate deeply into and effectively treat the soft tissues (e.g., muscle and ligamentous tissues), instead of being limited to the overlying dermal regions. Alternatively, for certain diseases or conditions it may be preferable to apply the composition by injecting this directly into or adjacent to the affected soft tissues.

As will be described in greater detail below, it is believed that the therapy of the present invention may be applicable to the treatment of a variety of disease conditions and states in addition to the musculoskeletal diseases to which the preferred embodiment is primarily directed.

b. Therapeutic Composition

As noted above, the therapeutic composition of the present invention is a combination of a mobilizing agent and a suitable antibiotic or other antimicrobial compound.

The mobilizing agent acts in the manner of a carrier and is preferably PLO gel for most topical applications. PLO gel has previously been used with certain nonsteroidal anti-inflammatory agents (such as Diclofenac) in the treatment of arthritic joints, where the PLO gel has enabled the anti-inflammatory agents to enter the dermis and blood stream. When used in combination with a suitable antibiotic in the compositions and methods of the present invention, however, it has been found that the PLO gel enables the antibiotic to penetrate not just the skin and subcutaneous tissues, but also much more deeply, so that the antibiotic enters into the ligamentous tissues, synovia and joints that are involved with the suspected chronic Chlamydia Pneumoniae and/or Mycoplasma infection; it is believed that the lipid component of the PLO gel may play a significant role in the deep, sub-dermal penetration which is achieved using the present invention. Similarly, it is believed that the PLO gel will enable the antibiotic to effectively penetrate soft tissues where the composition is applied internally, as by injection into the affected area. PLO gel suitable for use in the composition of the present invention is available from Gallipot Inc. (2020 Silver Bell Rd., St. Paul, Minn. 55122) under the designation "Pluronic-127NF Gel".

While organic hydrogels, and PLO gel in particular, are believed to be most effective for use in combination with azithromycin for topical application, other suitable gels may include, but are not limited to, the following: starch glycerite, bentonite magma, liquid-solid emulsion gel, lubricating gel formula, clear aqueous gel with dimethicone, poloxamer gel base, methylcellulose gel, alcoholic gel, and other organic gels, inorganic gels, hydrogels and organogels. Furthermore, while a gel-type composition is generally preferable from the standpoint of effectiveness and ease of use, it will be understood that in some embodiments the mobilizing agent-antimicrobial composition of the present invention may be prepared in the form of a suitable ointment, cream or paste for topical application, or in the form of a fluid or solution for internal use.

The second component of the system is the antimicrobial compound. As was noted above, the antimicrobial compound is preferably selected on the basis of its effectiveness against the target microorganism. Azithromycin (azithromycin dihydrate) is preferred for treatment of musculoskeletal disease, due to its known effectiveness against the Mycroplasma and Chlamydia organisms that are believed to be responsible for these conditions, Azithromycin has a high intracellular/extracellular concentration ratio (Aubert et al., Pulm Pharmacol Ther, 1998; 11(4):263–9), and also has been found to cooperate effectively with the preferred PLO gel component. Azithromycin suitable for use in the present invention is available from Pfizer Inc. (235 E 42$^{nd}$ Street, New York, N.Y. 10017) under the trademark "ZITHROMAX™".

It will be understood, however, that other suitable antibiotic/antimicrobial compounds may be used in combination with, or in place of, azithromycin, particularly where it has been determined that such other compounds are effective against a particular microorganism. Other suitable antibiotic compounds may include other members of the macrolide antibiotic family, such as erythromycin and clarithromycin, as well as other antibiotics known or believed to be effective against Chlamydia Pneumoniae, Mycoplasma and similar organisms. These include, but are not limited to, the following: moxifloxacin, minocycline, rifampin, doxycycline, ofloxacin, roxithromycin, coarithromycin, grepafoaxcin, luvofloxacin and trovafloxacin. Trovafloxacin should be considered with caution in view of some reports of hepatic toxicity. Grepafloxacin, rifanpin and moxifloxacin have been reported to have good potency again Chlamydia Pneumoniae. Particular synergy against C. Pneumoniae has been reported with the concurrent use of three antibiotics (rifampin, azythromycin, and ofloxacin or doxycycline), thus suggesting that this or other combinations of multiple antibiotics may be especially effective in some embodiments of the present invention. The macrolide antibiotics are generally preferred in that they exhibit anti-inflammatory effects in addition to performing antibiotic functions; particularly suitable are erythromycin and roxithromycin (Rulid™) the latter yielding similar results to azithromycin and having the advantage of a much lower cost.

As a group, macrolide antibiotics are typically characterized by a macrocyclic lactone ring, and other suitable members of the class may be employed in the present invention in addition to the examples listed above. Furthermore, other suitable antimicrobial compounds will occur to those skilled in the relevant art.

A third component of the therapeutic composition of the present invention is a penetration-enhancing adjuvant. The purpose of this component is to increase and expedite penetration into the soft tissues, and also to maintain the fluid consistency of the gel-antibiotic composition, and it may be considered optional in the sense that it may not be present in all embodiments of the invention. The preferred penetration-enhancing adjuvant for use with the combination of PLO and azithromycin described above is d-limonene, which is available in suitable form from many sources, including the aforementioned Gallipot Inc. Other suitable penetration enhancers may include, but are not limited to, various other terpenes, such as menthone, terpinen-4-ol and alpha-terpineol, for example, as well as decyl-methyl sulfoxid and DMSO.

c. Example Formulations

One preferred formulation, using the preferred combination of PLO gel and azithromycin, is prepared by the compounding of 250 mg of the azythromycin with 1 cc of PLO gel, with the azithromycin being reduced to a fine powder in a rolling mill before being mixed with the PLO. This forms a topical gel that has been found effective against chronic and acute pain from chronic tendonitis, bursitis, scars, synovitis and neuritis, when applied sparingly to the skin in the affected area three times a day over the course of a week.

A mixture of 250 mg azythromycin in 3 cc PLO (giving a concentration of approximately 83 mg/cc) was found to give results that were much weaker but still clinically significant. Extrapolating from this information, it is believed that the lower limit in terms of providing meaningful therapy when applied topically is approximately 50 mg azythromycin per 1 cc of PLO.

The practical upper limit (for topical application) is approximately 3 gm of azythromycin per 1 cc of PLO carrier. Above this limit, the composition tends to lose its gel consistency, and insufficient PLO may be present to ensure effective penetration of the underlying soft tissues. Similar effective ranges are anticipated when using erythromycin and roxithromycin. When the azythromycin or other antibiotic agent is used in relatively high concentrations, liquid d-limonene or other adjuvants may be used to thin the mixture and prevent it from becoming too thickly pasty.

Dosages and ratios may vary from the examples given above, based on the characteristics of the specific compounds that are included, the condition that is being treated, or other relevant factors.

d. Clinical Results

Approximately 68 patients were treated clinically for a variety of musculoskeletal disease conditions, including lateral epicondylitis, bursitis, carpel tunnel syndrome, degenerative joint disease of the knee, flexor tenosynovitis (trigger finger) and extensor tenosynovitis (DeQuervain's stenosing tenosynovitis), using the example formulation and regimen described above, i.e., 250 mg azythromicin compounded with 1 cc PLO, applied topically three times a day over a week period.

As a group, the patients demonstrated excellent response to the therapy. A number of patients who were being treated for work-related disabilities improved to the point where they spontaneously quit wearing their splints and asked to arrange for their return to work. In symptomatic total joint replacement patients, the treatment promptly eliminated minor tenderness, pain and effusion that had been chronically present for years. In other patients, post-operative scars became non-tender and non-swollen after one or two days of treatment. Early reflex sympathetic dystrophies were also successfully "turned off" in a matter of days using the therapy.

On average, approximately 2–3 weeks of treatment were required in order to attain the maximum extent of improvement, and no recurrence has been observed following cessation of the treatment. The treatment was found to be effective in the case of both chronic and acute conditions, although the latter responded most favorably if treated promptly after the onset of the symptoms.

To give a typical example, a 66 year-old male patient who was being seen in connection with a workman's compensation claim related that he could sit in comfort for the first time in approximately 12 years after undergoing one week of the therapy described above. This individual had been seen by an HMO for chronic bursitis, and surgery had been advised following an MRI and after physical therapy had yielded no relief. The patient applied the gel formulation to his shoulder (apparently, a subacromial bursitis) for three days, and the pain promptly disappeared and has yet to recur.

As further examples, numerous workman's compensation injury patients as well as private patients have had rapid and striking relief of pain with the PLO-macrolide gel, including the following:

A commercial airline pilot with work related chronic subacromial bursitis of the shoulder that resolved within days of the use of the gel composition of the present invention.

Two workman's compensation related chronic coccygeal pain patients who had resolution of their pain within days of using the same gel composition. A workman's compensation clerical worker with rapid amelioration of her chronic lateral epicondylitis with the gel.

Rapid relief of ulnar neuritis in a workman's compensation manual laborer.

Relief of chronic ankle tenosynovitis in an investment banker.

Rapid relief of chronic bursitis of the knee in a workman's compensation related injured to store manager.

Relief of medial compartment pain and tenderness secondary to osteoarthritis in several patients.

Rapid relief of extensor tenosynovitis in a work related injury in an assembly worker.

Immediate postoperative and prolonged relief of lower back pain after injection of liposomal azithromycin after a minimally invasive selective endoscopic discectomy of the lumbar spine.

The therapy of the present invention was also observed to be effective in clinical treatment of cervical/lumbosacral disc disease. On two occasions, azithromycin was applied with a liposome and another anti-inflammatory, a surgical arthroscopy of the intervertebral disc with good and immediate relief of the patients' severe pain. These results are consistent with applicant's observation that the majority of patients with symptomatic cervical or lumbosacral disc disease test positive on serum forensic Chlamydia Pneumoniae PCR DNA analysis, indicating an active systemic infection with the bacteria.

A factor that may relate to the observed results with respect to disc disease is the presence of neurotoxic phospholipase A2 in the affected tissue. Chlamydia Pneumoniae stimulates the release of phospholipase A2 from white cells, as do several other gram negative bacteria (see Menschikowski et al, *Arteriosclerosis, Thrombosis, and Vascular Biology*, March 2000). In addition, the cell membrane of Chlamydia Pneumoniae includes a component which itself is a phospholipase, i.e., Outer Membrane Phospholipase A (see Decker, *Molecular Microbiology*, February 2000). Phospholipase A2 (which, incidentally, is the class of chemical present in neurotoxic snake venom) has been found in high concentrations in symptomatic lumbar discs, along with acidic pH levels, and the very low oxygen partial pressures present in the intervertebral disc may further potentiate the destructive effects of the phospholipase. Azithromycin appears to have a direct effect in mitigating the effects of this neurotoxic substance (see VanBebeke et al, *European Journal of Pharmacology*, October 1994), and so this may be a mechanism contributing to the relief that is provided by the therapy of the present invention.

e. Treatment of Additional Diseases/Conditions

The above description has focused on the treatment of various musculoskeletal conditions in accordance with the preferred embodiment of the present invention. It is believed, however, that the therapy of the present invention may be applied to a wide variety of other disease states/conditions that stem from soft tissues being involved in an active infection by Chlamydia Pneumoniae, Mycoplasma, or other microorganisms.

For example, Chlamydia Pneumoniae has been strongly implicated in coronary artery. occlusive disease and other forms of arteriosclerosis (the finding of positive C. Pneumoniae serum DNA PCR has been linked to active coronary occlusive disease, and the phospholipase A2 material described above has been linked to acute hypoxic pulmonary arterial pressure (see Lee et al, *Sheng Li Hsueh Pao*, December 1997)), and in asthma, multiple sclerosis and Alzheimer's Disease. It is therefore believed that the combination of azythromycin or other antibiotics with PLO gel or other mobilizing agents may be effective in arresting or effecting a cure to certain of these diseases.

In the case of arteriosclerosis, multiple sclerosis, Alzheimer's Disease and similar conditions, the therapeutical composition may be administered intravenously or intrathecally (i.e., in the spinal fluid), assuming that the toxicology of the composition is found to be acceptable for such use. Similarly, if the PLO-azithromycin combination (or another formulation in accordance with the present invention) is proven safe for use in an inhaler, this may provide an effective treatment for asthma, chronic sinusitis (which has also been closely linked to C. Pneumoniae), and soft palate hypertrophy and related conditions that are largely responsible for snoring and sleep apnea. As with the other conditions described above, the chief advantage would be to effectively penetrate the affected soft tissues and attack the bacteria deep inside the tissues.

Chlamydia Pneumoniae is also suspected as a cause of some forms of obesity. Specifically, circulating serum HSP60 and HSP10 produced as a result of a Chlamydia infection is suspected of modifying the body's metabolism so that this prioritizes the creation of fat, thereby rendering weight loss difficult or impossible for many people. Systematic eradication of the infection using the PLO-azythromycin combination or other formulation in accordance with the present invention may make relatively effortless weight loss a possibility for such individuals.

In addition to be used as a "stand alone" treatment, the therapy of the present invention may be combined with other treatment methodologies in order to increase the speed and effectiveness of the control/eradication process. For example, hyperbaric oxygen therapy, in which the patient breathes 100% oxygen at 2–3 atmospheres of increased pressure, has been shown to effectively suppress the growth of Chlamydia Pneumoniae and Mycoplasma C. Pneumoniae has been detected (by PCR) in approximately 97% of the spinal fluid samples of multiple sclerosis patients (in research conducted at Vanderbilt University), and in separate research in Great Britain approximately 13,000 multiple sclerosis patients have been treated themselves empirically with periodic hyperbaric oxygen therapy, with an apparent arrest of multiple sclerosis symptoms in many cases. Hyperbaric oxygen therapy may therefore be a useful adjunctive therapy for use in combination with the present invention to control or eradicate chronic C. Pneumoniae and Mycoplasma infections.

It is to be recognized that various alterations, modifications, and/or additions may be introduced into the constructions and arrangements of parts described above without departing from the spirit or ambit of the present invention.

What is claimed is:

1. A method for alleviating a disease state resulting from a microbial infection affecting musculoskeletal soft tissue, said method comprising the steps of:

determining a localized area of a patient's body in which affected musculoskeletal soft tissue is located; providing a treatment composition comprising, in combination:

(i) a selected macrolide antibiotic; and (ii) a selected mobilizing agent in an amount sufficient to enable said macrolide antibiotic to penetrate into said musculoskeletal soft tissue; and applying said treatment composition to said localized area of said patient's body so that said macrolide antibiotic penetrates said affected musculoskeletal soft tissue so as to reach said microbial infection therein.

2. The method of claim 1, wherein the step of applying said treatment composition comprises:

applying said treatment composition topically to a skin area overlying said musculoskeletal soft tissue in said predetermined area of the body.

3. The method of claim 1, wherein the step of applying said treatment composition comprises:

applying said treatment composition by hypodermic injection into said musculoskeletal soft tissue in said area of the body.

4. The method of claim 1, wherein said treatment composition further comprises:
   a penetration enhancing adjuvant.

5. The method of claim 4, wherein said penetration enhancing adjuvant comprises d-limonene.

6. A method of alleviating a disease state resulting from a microbial infection affecting sub-dermal soft tissue in a predetermined area of the body, said method comprising the steps of:
   Providing a treatment composition comprising, in combination:
      (i) a macrolide antibiotic macrolide antibiotic selected from the group consisting of azithromycin, erythromycin and roxithromycin; and
      (ii) PLO gel in an amount sufficient to enable said macrolide antibiotic to penetrate into said sub-dermal soft tissue; and
   applying said treatment composition to said predetermined area of the body so that said macrolide antibiotic penetrates said sub-dermal soft tissues so as to reach said microbial infection therein.

7. The method of claim 6, wherein said treatment composition further comprises:
   a penetration enhancing adjuvant.

8. The method of claim 7, wherein said penetration enhancing adjuvant comprises d-limonene.

9. A method for alleviating a disease state resulting from a microbial infection affecting sub-dermal soft tissue in a predetermined area of the body, said method comprising the steps of:
   providing a treatment composition comprising, in combination:
      (i) a selected macrolide antibiotic;
      (ii) a selected mobilizing agent in an amount sufficient to enable said macrolide antibiotic to penetrate into said sub-dermal soft tissue; and
      (iii) a penetration enhancing adjuvant comprising limonene; and
   applying said treatment composition to said predetermined area of the body so that said macrolide antibiotic penetrates said sub-dermal soft tissue so as to reach said microbial infection therein.

10. The method of claim 9, wherein the step of applying said treatment composition comprises:
    applying said treatment composition topically to a skin area overlying said sub-dermal soft tissue in said predetermined area of the body.

11. The method of claim 9, wherein the step of applying said treatment composition comprises:
    applying said treatment composition by injection into said sub-dermal soft tissue in said area of the body.

12. The method of claim 9, wherein the step of providing said treatment composition comprises:
    selecting said macrolide antibiotic from the group consisting of azithromycin, erythromycin and roxithromycin.

13. The method of claim 12, wherein said mobilizing agent comprises a gel compound.

14. The method of claim 13, wherein said gel compound is PLO gel.

15. A treatment composition for alleviating a disease state resulting from a microbial infection affecting musculoskeletal soft tissue in a predetermined area of the body, said treatment composition comprising:
    (i) a macrolide antibiotic selected from the group consisting of azithromycin, erythromycin and roxithromycin; and
    (ii) PLO gel in an amount sufficient to enable said macrolide antibiotic to penetrate into said musculoskeletal soft tissue so as to reach said microbial infection therein when said composition is applied to said predetermined area of the body.

16. The treatment composition of claim 15, further comprising:
    (iii) a selected penetration enhancing adjuvant for increasing penetration of said musculoskeletal soft tissue in said predetermined area of the body.

17. The treatment composition of claim 16, wherein said penetration enhancing adjuvant comprises d-limonene.

18. A treatment composition for alleviating pain and inflammation resulting from a microbial infection affecting sub-dermal musculoskeletal tissue in a predetermined area of the body, said treatment composition comprising:
    (i) a macrolide antibiotic compound selected from the group consisting of azithromycin, erythromycin and roxithromycin; and
    (ii) PLO gel in an amount sufficient to enable said macrolide antibiotic compound to penetrate into said sub-dermal soft tissue so as to reach said microbial infection therein when said composition is applied topically to said predetermined area of the body.

19. The treatment composition of claim 18, wherein said macrolide antibiotic compound is present in said composition in an amount in the range from about 50 mg/cc of PLO gel to about 3 gm/cc of PLO gel.

20. The treatment composition of claim 19, wherein said macrolide antibiotic compound is azithromycin.

21. The treatment composition of claim 20, wherein said azithromycin is present in said composition in an amount of about 250 mg/cc of PLO gel.

22. The treatment composition of claim 18, further comprising:
    a selected penetration enhancing adjuvant for increasing penetration of said macrolide antibiotic compound into said sub-dermal soft tissue.

23. The treatment composition of claim 22, wherein said penetration enhancing adjuvant comprises d-limonene.

24. A treatment composition for alleviating a disease state resulting from a microbial infection affecting musculoskeletal soft tissue in a predetermined area of the body, said treatment composition comprising:
    (i) azithromycin; and
    (ii) PLO get in an amount sufficient to enable said azithromycin to penetrate into said soft tissue so as to reach said microbial infection therein when said composition is applied to said predetermined area of the body.

25. The treatment composition of claim 24, further comprising:
    a selected penetration enhancing adjuvant for increasing penetration of said sub-dermal soft tissue in said predetermined area of the body.

26. The treatment composition of claim 25, wherein said penetration enhancing adjuvant comprises d-limonene.

27. A treatment composition for alleviating a disease state resulting from a microbial infection affecting sub-dermal soft tissue in a predetermined area of the body, said treatment composition comprising:
    (i) a selected macrolide antibiotic;
    (ii) a selected mobilizing agent in an amount sufficient to enable said macrolide antibiotic to penetrate into said sub-dermal soft tissue so as to reach said microbial infection therein when said composition is applied to said predetermined area of the body; and (iii) a selected penetration enhancing adjuvant for increasing penetration of said sub-dermal soft tissue in said predetermined area of the body, said penetration enhancing adjuvant comprising d-limonene.

28. The treatment composition of claim 27, wherein said macrolide antibiotic composition is selected from the group consisting of azithromycin, erythromycin and roxithromycin.

29. The treatment composition of claim 28, wherein said macrolide antibiotic compound is azithromycin.

30. The treatment composition of claim 28, wherein said mobilizing agent comprises a selected organogel compound.

31. The treatment composition of claim 30, wherein said organogel compound is PLO gel.

* * * * *